US012758313B2

(12) United States Patent
Lenich et al.

(10) Patent No.: US 12,758,313 B2
(45) Date of Patent: Oct. 13, 2026

(54) PLANNING THERAPEUTIC ULTRASOUND TREATMENT

(71) Applicant: Siemens Healthcare GmbH, Erlangen (DE)

(72) Inventors: Tobias Lenich, Nuremberg (DE); Alois Regensburger, Poxdorf (DE)

(73) Assignee: Siemens Healthineers AG, Forchheim (DE)

( * ) Notice: Subject to any disclaimer, the term of this patent is extended or adjusted under 35 U.S.C. 154(b) by 944 days.

(21) Appl. No.: 17/973,475

(22) Filed: Oct. 25, 2022

(65) Prior Publication Data

US 2023/0126520 A1 Apr. 27, 2023

(30) Foreign Application Priority Data

Oct. 26, 2021 (DE) ..................... 10 2021 212 077.6

(51) Int. Cl.
*A61B 34/10* (2016.01)
*A61N 7/02* (2006.01)

(52) U.S. Cl.
CPC ................ *A61B 34/10* (2016.02); *A61N 7/02* (2013.01); *A61B 2034/104* (2016.02); *A61B 2034/105* (2016.02)

(58) Field of Classification Search
CPC .............. A61B 34/10; A61B 2034/104; A61B 2034/105; A61N 7/02
See application file for complete search history.

(56) References Cited

U.S. PATENT DOCUMENTS

2002/0111552 A1 8/2002 Maor et al.
2004/0009459 A1 1/2004 Anderson et al.
(Continued)

FOREIGN PATENT DOCUMENTS

DE 102011002928 A1 7/2012
DE 102021208498 A1 2/2023
(Continued)

OTHER PUBLICATIONS

Qu, Shibin, et al. "Non-thermal histotripsy tumor ablation promotes abscopal immune responses that enhance cancer immunotherapy." Journal for immunotherapy of cancer 8.1 (2020).

*Primary Examiner* — Sean A Frith
(74) *Attorney, Agent, or Firm* — Lempia Summerfield Katz LLC

(57) ABSTRACT

According to a computer-implemented method for planning therapeutic ultrasound treatment of a three-dimensional tissue region, a tissue model containing a material parameter relating to deformability and/or elasticity of a corresponding material of the tissue region is provided in spatially resolved and/or directionally resolved form. Based on the tissue model, part of the tissue region is determined as a treatment region, and, depending on the tissue model and the treatment region, a therapeutic plan is generated to change the at least one material parameter. The therapeutic plan includes at least one characterization parameter that characterizes a plurality of lesions with respect to spatial arrangement and/or pose and/or shape and/or at least one configuration parameter of the plurality of lesions for a therapeutic ultrasound apparatus for generating the plurality of lesions.

17 Claims, 1 Drawing Sheet

(56) References Cited

U.S. PATENT DOCUMENTS

| | | | | |
|---|---|---|---|---|
| 2007/0219448 | A1* | 9/2007 | Seip | A61N 7/02 600/453 |
| 2010/0317971 | A1* | 12/2010 | Fan | G01S 15/8993 600/439 |
| 2012/0190962 | A1 | 7/2012 | Glaser-seidnitzer et al. | |
| 2015/0010222 | A1* | 1/2015 | Provost | A61B 8/085 382/131 |
| 2019/0000422 | A1* | 1/2019 | West | G01S 7/52042 |
| 2019/0090951 | A1* | 3/2019 | Camus | A61B 8/483 |
| 2021/0210189 | A1* | 7/2021 | Casey | B29C 64/393 |
| 2022/0183560 | A1 | 6/2022 | Aeschlimann et al. | |
| 2022/0354597 | A1* | 11/2022 | Kaouk | A61B 34/30 |
| 2023/0039242 | A1 | 2/2023 | Regensburger et al. | |

FOREIGN PATENT DOCUMENTS

| | | | |
|---|---|---|---|
| WO | 02058791 | A1 | 8/2002 |
| WO | 2020193667 | A2 | 10/2020 |

* cited by examiner

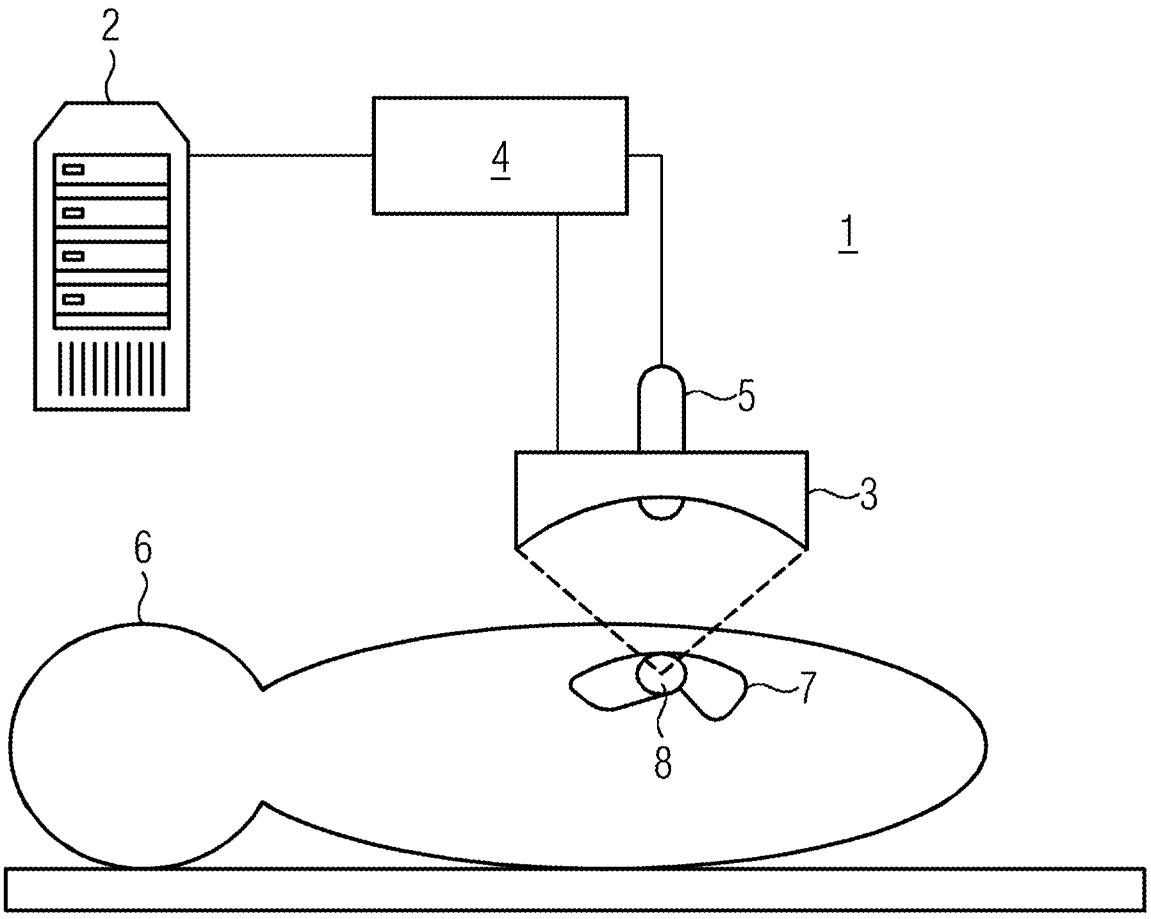
2
4
1
5
3
6
7
8

PLANNING THERAPEUTIC ULTRASOUND TREATMENT

This application claims the benefit of German Patent Application No. DE 10 2021 212 077.6, filed on Oct. 26, 2021, which is hereby incorporated by reference in its entirety.

BACKGROUND

The present embodiments relate to planning therapeutic ultrasound treatment of a three-dimensional tissue region.

Histotripsy is a method for therapeutic ultrasound treatment that may be used for non-invasive tumor ablation, as described, for example, in the publication by Q. Shibin et al. “Non-thermal histotripsy tumor ablation promotes abscopal immune responses that enhance cancer immunotherapy,” Journal for ImmunoTherapy of Cancer, 8 (1), 2020.

Herein, high-intensity ultrasound pulses that converge in a region of focus generate extreme pressure differences resulting in the destruction of the cell structure and corresponding lesions in the tissue. Histotripsy uses ultrasound pulses with a duration in the microsecond range in order to mechanically homogenize the tissue. Pauses in the order of milliseconds or longer between the ultrasound pulses enable undesirable heat generation to be avoided.

For example, when the patient moves, tissue with low elasticity or deformability (e.g., tumor tissue, cartilage, scar tissue, tendons, muscles, fascia, and so on) may act on surrounding tissue or vessels, and this may limit the function of the surrounding tissue, for example, by limiting blood flow through a vessel, or mobility of the patient may be limited or painful. Low elasticity or deformability may also lead to fractures, tears, or other types of damage to anatomical structures (e.g., in the case of mechanical impact). Therefore, selective modification of elasticity or deformability may be desirable.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a possible way for selectively influencing elasticity or deformability of tissue is provided.

The present embodiments are based on the idea of automatically creating a therapeutic plan for therapeutic ultrasound treatment based on a three-dimensional tissue model. Herein, the therapeutic plan includes information on how the therapeutic ultrasound apparatus may be used to selectively change at least one material parameter relating to deformability and/or elasticity of the corresponding material of a tissue region.

Therapeutic ultrasound treatment may, for example, encompass histotripsy therapy, high-intensive focused ultrasound (HIFU) therapy, or low-energy focused ultrasound (LOFU) therapy. The present document mainly addresses histotripsy therapy, but this should always be understood to be representative of other types of therapeutic ultrasound treatment.

One aspect of the present embodiments discloses a computer-implemented method for planning therapeutic ultrasound treatment (e.g., histotripsy therapy) of a three-dimensional tissue region. Herein, a three-dimensional tissue model (e.g., a deformable three-dimensional tissue model) of the tissue region is provided in computer-readable form. The tissue model contains at least one material parameter relating to deformability and/or elasticity of the corresponding material of the tissue region in spatially resolved and/or directionally resolved form. Based on the tissue model (e.g., based on the at least one material parameter), part of the tissue region is determined as a treatment region. Depending on the tissue model and the treatment region (e.g., depending on the at least one material parameter in the treatment region and optionally in parts of the tissue region outside the treatment region), a therapeutic plan is generated for therapeutic ultrasound treatment in order to change the at least one material parameter in a predefined manner. Herein, the therapeutic plan contains at least one configuration parameter for a therapeutic ultrasound apparatus (e.g., a histotripsy apparatus) for generating a plurality of lesions, and/or the therapeutic plan contains at least one characterization parameter. The at least one characterization parameter characterizes the plurality of lesions that may be generated by the therapeutic ultrasound apparatus in the treatment region with respect to spatial arrangement of the plurality of lesions and/or respective pose of the plurality of lesions and/or respective shape of the plurality of lesions.

Unless specified otherwise, all the acts of the computer-implemented method may be performed by at least one computing unit. For example, a data processing apparatus including at least one processor that is configured or adapted to perform a computer-implemented method according to the present embodiments may perform the acts of the computer-implemented method. For this purpose, the data processing apparatus, which may correspond to the at least one computing unit, may, for example, store a computer program including instructions that, when executed by the data processing apparatus (e.g., the at least one processor, cause the data processing apparatus to execute the computer-implemented method.

A computing unit may, for example, be understood to be a data processing device containing a processing circuit. Therefore, the computing unit may, for example, process data for performing computing operations. This may also include operations for performing indexed access to a data structure (e.g., a look-up table (LUT)).

The computing unit may, for example, contain one or more computers, one or more microcontrollers, and/or one or more integrated circuits (e.g., one or more application-specific integrated circuits (ASICs)), one or more field-programmable gate arrays (FPGAs), and/or one or more systems on a chip. The computing unit may also contain one or more processors (e.g., one or more microprocessors, one or more central processing units (CPUs), one or more graphics processing units (GPUs), and/or one or more signal processors, such as one or more digital signal processors (DSPs)). The computing unit may also include a physical or virtual network of computers or any of the other units mentioned.

In various exemplary embodiments, the computing unit includes one or more hardware and/or software interface and/or one or more memory units.

A memory unit may be configured as a volatile data memory (e.g., a dynamic random access memory (DRAM) or static random access memory (SRAM)) or as a non-volatile data memory (e.g., a read-only memory (ROM), programmable read-only memory (PROM), erasable read-only memory (EPROM), electrically erasable read-only memory (EEPROM), flash memory or flash EEPROM, ferroelectric random access memory (FRAM), magnetoresistive random access memory (MRAM), or phase-change random access memory (PCRAM)).

The tissue model may, for example, be configured as a three-dimensional voxel model or a model of other three-dimensional volume elements or as a three-dimensional surface model, which is, for example, defined by a polygon mesh. The at least one material parameter is then stored for each volume or surface element so that spatially resolved provision of the at least one material parameter is achieved. In addition, the at least one material parameter may also be stored in a direction-dependent manner (e.g., in the form of a tensor with one dimension for each of three spatial directions) for each volume or surface element so that spatial resolution and directional resolution are obtained. Herein, the volume or surface elements may have a different (e.g., partially or completely) or identical spatial extent and/or shape.

In other exemplary embodiments, however, spatial resolution may be partially or completely omitted, and only directional resolution implemented. For example, various regions of the tissue region may be segmented, and the at least one material parameter may be stored for each segment in a directionally dependent, but spatially constant, form. The spatial resolution is then restricted to possible differences in the at least one material parameter for different segments. If only one segment is present in the tissue region under consideration, the tissue model may also be provided exclusively as a directionally resolved and non-spatially resolved model.

The model may be generated in different ways. For example, it is possible to use empirical information that estimates typical spatially dependent and/or directionally dependent distributions of the at least one material parameter for the corresponding tissue region. Alternatively or additionally, it is possible for specific information from imaging methods (e.g., magnetic resonance tomography (MRT) images or computed tomography (CT) images or ultrasound images) to be used to generate the model. With such imaging methods, the intensity distribution on the corresponding images may be influenced by the at least one material parameter (e.g., in the case of MRT imaging). For example, the at least one material parameter may be measured directly or indirectly, at least in part.

In some embodiments, the tissue model may be provided as a deformable tissue model. This may, for example, be understood as providing that the geometric shape of the tissue region or of parts of the tissue region may be changed (e.g., elastically), for example, to simulate or emulate a movement of the patient. The at least one material parameter may then, for example, also be provided in time resolved form relating to one or more predefined movements of the patient or the tissue region.

The at least one material parameter relates to the deformability and/or elasticity of the corresponding material. Deformability may, for example, be defined by the resistance of the tissue with which the tissue may resist a change to its external shape (e.g., when the tissue is bent, compressed, or stretched). Elasticity is not necessarily linked to a change to the external shape and may possibly only take effect in the interior of the tissue region on exposure to a mechanical force or stress.

For example, the at least one material parameter may contain a modulus of elasticity, a shear modulus, and/or a bulk modulus, in corresponding embodiments (e.g., in three spatial directions or as a tensor).

The objective of the therapeutic plan is to change the at least one material parameter in a predefined manner. This provides that the at least one material parameter would be changed in the predefined manner or changed approximately in the predefined manner if the therapeutic ultrasound treatment according to the therapeutic plan were performed on an actual patient or in the form of a simulation on the tissue model (e.g., if the plurality of lesions were generated or simulated according to the at least one characterization parameter and/or the at least one configuration parameter).

Herein, the change in the material parameter may be explicitly quantified as the objective of the generation of the lesions, or the change in one or more variables that are dependent on the material parameter may be quantified as the objective of the generation of the lesions. Possible examples of such variables are mechanical forces, mechanical stresses, restricted movements, or the like, that, in static cases or in the case of movements of the tissue region, occur in or act on the tissue region. Since the at least one material parameter relates to elasticity and/or deformability, a change in the at least one material parameter is accompanied by a change in these variables (e.g., the mechanical forces or stresses).

Herein, although the change in the at least one material parameter may be understood as the cause of the change in the dependent variable, the objective of the generation of the lesions may still be formulated in the form of an objective for the dependent variable (e.g., in the form of a cost function for optimizing the dependent variable in a statistical optimization procedure or when using an artificial neural network to determine the therapeutic plan).

The respective pose of a lesion includes the corresponding position of the lesion or a specific point of the lesion (e.g., the center of the lesion) in a prespecified global coordinate system and optionally the orientation of this lesion in the coordinate system, if such an orientation may be defined, which ultimately also depends on the shape of the lesion. The orientation of the lesion may, for example, be defined by an axis of the lesion (e.g., a major axis and/or axis of symmetry). The shape of the lesion may, for example, be defined by a three-dimensional geometric figure. The shape of the lesion may, for example, be represented by a sphere, an ellipsoid, a cylinder, a torus, or another shape. Herein, the shape and/or pose of the respective lesions may be target specifications for the therapeutic ultrasound treatment.

Alternatively or additionally to defining the respective shapes and/or poses of the individual lesions, the at least one characterization parameter may also specify the spatial arrangement of the totality of the plurality of lesions in the treatment region (e.g., also as a target specification for the therapeutic ultrasound treatment). The at least one characterization parameter may, for example, include distances between adjacent lesions, their relative position with respect to one another, their spatial density, and so on. Alternatively or additionally, the at least one characterization parameter may include or specify an overall shape or extent to be achieved by the plurality of lesions. For example, an external shape for the arrangement of the plurality of lesions may be specified. The at least one characterization parameter may also specify a porosity of the tissue in the treatment region to be achieved by the plurality of lesions (e.g., a ratio of the volume corresponding to lesions to the volume of the remaining tissue).

The at least one characterization parameter (e.g., the spatial arrangement of the plurality of lesions and the poses and shapes of the individual lesions) may be spatially constant in the treatment region or may change depending on the location. Herein, continuous changes are just as conceivable as values for the at least one characterization parameter that vary by region or section. For example, the at least one material parameter may be modified very flexibly.

The spatial arrangement of the plurality of lesions is not necessarily independent of the shapes and/or poses of the individual lesions. Specifying the position and/or orientation of the individual lesions in absolute form in the global coordinate system also indirectly determines the arrangement of the totality of lesions, at least in part. The specification of the arrangement of the plurality of lesions may possibly also restrict the shape and/or pose of the individual lesions. Accordingly, the at least one characterization parameter may specify only the arrangement or only the shape and/or pose of the individual lesions. Alternatively, the at least one characterization parameter may partially specify the arrangement of the plurality of lesions and partially specify the shape and/or pose of the individual lesions such that the components of the at least one characterization parameter are consistent overall.

While the at least one characterization parameter relates directly to the definition of the lesions, the at least one configuration parameter specifies the technical configuration of the therapeutic ultrasound apparatus (e.g., the histotripsy apparatus) that may be specified for generating the lesions. Therefore, the configuration parameter may, for example, include a pulse duration and/or pulse amplitude of the ultrasonic waves generated by the therapeutic ultrasound apparatus for generating the lesions, a focus shape or a focus alignment of the ultrasonic waves, an arrangement of one or more ultrasonic transducers of the therapeutic ultrasound apparatus (e.g., one or more ultrasound sources for generating the ultrasonic waves) with respect to the tissue region, and so on. The one or more ultrasonic transducers may, for example, include a row or matrix array of ultrasound transducers.

The at least one configuration parameter may also relate to a trajectory for guiding the region of focus of the ultrasonic waves (e.g., a writing trajectory for generating the lesions). For example, the at least one characterization parameter may include the specific trajectory and/or a direction of movement of the region of focus, a speed of movement of the region of focus, or the like.

Therefore, the provision of the therapeutic plan provides a specific specification for the therapeutic ultrasound apparatus or a user of the therapeutic ultrasound apparatus on the basis of which the therapeutic ultrasound therapy may be performed in order to influence or change the material parameter in the desired predefined manner; this is accompanied by the advantages explained in the introduction of such a change in the at least one material parameter (e.g., the elasticity and/or deformability of the tissue).

The therapeutic plan may be provided prior to the initial performance of the therapeutic ultrasound therapy on the patient so that the initial performance of the therapeutic ultrasound therapy takes place based on the therapeutic plan provided according to the present embodiments. Initial therapeutic ultrasound therapy may, however, also have been performed previously according to an initial therapeutic plan. The initial therapeutic plan may, for example, have been generated based on an initial tissue model (e.g., also in the manner according to the present embodiments or in another manner). After the performance of the initial therapeutic ultrasound therapy, the initial tissue model may be modified accordingly in order to generate the current tissue model. The subsequent performance of the method according to the present embodiments may then be based not only on the current tissue model, but also on the initial therapeutic plan and/or the initial tissue model for generating the current therapeutic plan. In this way, the objective (e.g., the corresponding influencing of the material parameter in the predefined manner) may be achieved iteratively and, accordingly, as precisely and completely as possible.

According to at least one embodiment of the computer-implemented method, based on the tissue model (e.g., based on the at least one material parameter), a load variable relating to a mechanical force acting on one or more parts of the tissue region and/or relating to a mechanical stress present in the tissue region is determined in a spatially resolved manner and/or in a directionally resolved manner. The treatment region is determined depending on the load variable determined in a spatially resolved manner and/or in a directionally resolved manner.

The load variable may, for example, be determined by performing a numerical simulation of the forces and/or mechanical stresses based on the tissue model (e.g., a simulation based on the finite element method (FEM)).

The load variable may, for example, be equal to the mechanical force or equal to the mechanical stress or calculated from the mechanical force and/or the mechanical stress.

Herein, the treatment region may be determined fully automatically (e.g., by comparing the load variable with one or more prespecified limit values). However, it is also possible to implement a semi-automatic determination of the treatment region in that a user specifies a point where the treatment region is suspected to be located, and the treatment region is then determined starting from the prespecified point, which may also be referred to as a seed point in this context.

According to at least one embodiment, the load variable is determined based on the tissue model (e.g., based on the at least one material parameter) and based on a predefined movement of the tissue region in a spatially resolved manner and/or in a directionally resolved manner.

The predefined movement is therefore, for example, simulated based on the tissue model (e.g., by deformation of the tissue model), and the force acting or stress present during the movement is analyzed (e.g., compared with corresponding limit values) in order to determine the treatment region. Herein, the movement may, for example, take place along one or more degrees of freedom of movement and/or along a predetermined movement trajectory.

The therapeutic plan for defining the lesions may then, for example, be generated such that the predefined influencing of the at least one material parameter is achieved during the corresponding movement or during a part of the movement (e.g., at an initial and/or final state of the movement). The therapeutic plan may also be determined such that the characterization parameters and/or configuration parameters may be coordinated with a specific state during the movement (e.g., an initial or final state of the movement) so that, therefore, the corresponding state may be set prior to the generation of the lesions and maintained during the generation of the lesions. In this way, the lesions may, for example, be generated in the state of minimum or maximum application of force or mechanical stress in the treatment region.

According to at least one embodiment, the load variable determined in a spatially resolved manner and/or in a directionally resolved manner is compared with a prespecified load limit, and the treatment region is determined as a part of the tissue region within which the load variable determined in a spatially resolved manner and/or in a directionally resolved manner is greater than the load limit.

Herein, the comparison may, for example, also be performed analogously individually for different spatial directions.

The treatment region may, for example, be determined such that the load variable in the entire treatment region is greater than the load limit. Alternatively, it is also possible for a tolerance range to be defined in which the load variable may be less than or equal to the load limit, but which is still defined as part of the treatment region.

In some embodiments, the treatment region may also be determined using a trained artificial neural network or another algorithm trained using machine learning. The algorithm may accordingly be trained to use the tissue model (e.g., the spatial information and the at least one material parameter) as input data to predict the treatment region. Accordingly, annotated training tissue models may be provided as training data, where the annotations are based on the corresponding treatment region that may then, for example, be manually defined.

According to at least one embodiment, the therapeutic plan is generated by minimizing the load variable by varying the at least one characterization parameter and/or the at least one configuration parameter.

In other words, the therapeutic plan is then determined by the characterization parameters and/or configuration parameters that minimize the load variable (e.g., the force and/or stress). It is, for example, possible to use a gradient descent method for minimization, where the load variable may, for example, serve as a cost function.

According to at least one embodiment, the load variable is reduced by varying the at least one characterization parameter and/or the at least one configuration parameter to a value that is smaller than a prespecified maximum load limit.

In other words, minimization may, for example, be terminated prematurely when the maximum load limit has been reached, which is then accordingly greater than the minimum value for the load variable.

Herein, the variation, minimization, or reduction of the load variable may also take account of one or more prespecified boundary conditions. For example, the shape and/or size and/or number of lesions may be limited. It is also possible for specific regions of the treatment region to be prespecified in which no lesions may be generated. It is also possible for a minimum distance to specific tissue regions or between the individual lesions to be prespecified. It is also possible for limitations of the therapeutic ultrasound apparatus (e.g., with respect to the at least one configuration parameter) to be taken into account.

Herein, in corresponding embodiments, the minimization or reduction of the load variable may also be coordinated with the predefined movement of the tissue region. For example, minimization or reduction may be performed during a specific part or at a specific state of the movement (e.g., at the initial state or final state of the movement).

According to at least one embodiment, a function trained by machine learning is applied to input data that is dependent on the tissue model and the treatment region (e.g., therefore, on the at least one material parameter in the treatment region and outside the treatment region in the tissue region) to generate output data. The output data determines the at least one characterization parameter and/or at least one configuration parameter. The therapeutic plan is generated depending on the output data.

Herein, the output data may be equal to the at least one characterization parameter and/or the at least one configuration parameter. Alternatively, the at least one characterization parameter and/or the at least one configuration parameter may be derived from the output data.

The trained function is, for example, provided by a trained artificial neural network. For example, known network architectures for optimization or regression procedures or generative adversarial networks (GAN) are suitable for this purpose.

Herein, the application of the trained function to the input data changes the at least one material parameter in the predefined manner, for example, by minimizing or reducing the load variable.

In embodiments in which the initial therapeutic ultrasound therapy according to the initial therapeutic plan has already been performed prior to the performance of the computer-implemented method for planning the therapeutic ultrasound therapy, the input data of the trained function may, for example, additionally be based on the initial therapeutic plan and/or the initial tissue model. This may improve accuracy in determining the therapeutic plan.

Accordingly, the trained function may be trained using a cost function that is directly or indirectly dependent on the at least one material parameter (e.g., on the mechanical forces and/or stresses in the tissue region). For example, the training may be performed using corresponding pairs of data sets each including, a tissue model and a corresponding set of characterization parameters and/or configuration parameters. In this way, the function may learn which characterization parameters and/or configuration parameters lead to which change of the material parameter.

According to at least one embodiment, the tissue model is modified according to the therapeutic plan. The load variable is determined again in a spatially resolved manner and/or in a directionally resolved manner based on the modified tissue model, and a further therapeutic plan for the therapeutic ultrasound therapy is generated depending on the load variable determined again in a spatially resolved manner and/or in a directionally resolved manner.

Herein, the further therapeutic plan analogously includes, for example, at least one further characterization parameter and/or at least one further configuration parameter as explained above for the therapeutic plan. In this way, it is therefore possible to implement an iterative procedure, where the change in the at least one material parameter in the predefined manner is achieved not in a single step, but in two or more steps, so that requirements with respect to the exactness of the tissue model may possibly be reduced.

According to at least one embodiment, the load variable determined again in a spatially resolved manner and/or in a directionally resolved manner is compared with the load limit, and the further therapeutic plan is generated depending on a result of the comparison and depending on the treatment region.

According to at least one embodiment, the load variable determined again in a spatially resolved manner and/or in a directionally resolved manner is compared with the load limit; a further part of the tissue region is determined as a further treatment region depending on a result of the comparison, and the further therapeutic plan is generated depending on the further treatment region.

In other words, this enables non-optimal determination of the treatment region in the first act or in the preceding act to be corrected.

According to at least one embodiment, the at least one material parameter includes a modulus of elasticity and/or a shear modulus and/or a bulk modulus, possibly in three spatial directions in each case.

According to at least one embodiment, the therapeutic plan is created such that the at least one characterization parameter characterizes an anisotropic distribution of the plurality of lesions.

In other words, this defines, for example, a preferred direction in order to selectively facilitate or limit movements of the tissue region (e.g., along the preferred direction or at a prespecified angle, such as a right angle, with respect to the preferred direction). The movements of the tissue region may also include rotation about the preferred direction.

According to at least one embodiment, the therapeutic plan is generated such that the at least one characterization parameter is generated in the form of a binary map for the treatment region. Herein, the binary map stores a first value (e.g., a logical 1) for positions at which one lesion of the plurality of lesions is provided and stores a second value (e.g., a logical 0) that is different than the first value for positions at which none of the plurality of lesions is provided. Herein, the number of positions prespecified for each lesion depends upon the resolution of the therapeutic ultrasound apparatus and on the size and shape of the lesions.

According to at least one embodiment, the therapeutic plan is created such that the at least one characterization parameter characterizes a distribution of the plurality of lesions over at least two subregions of the treatment region. The distribution differs in different ones of the at least two subregions.

This achieves a zonally different influence on the at least one material parameter, which may lead to a desired preference for specific directions of movement or the like. For example, individual subregions may also include no lesions.

According to at least one embodiment, the therapeutic plan is created such that the at least one characterization parameter characterizes an arrangement of the plurality of lesions and/or the respective shape and/or pose thereof in the at least two subregions, where the arrangement or the shapes and/or poses differ from one another in different ones of the at least two subregions.

According to at least one embodiment, image data depicting the tissue region of a patient to be examined is provided, and the tissue model is generated based on the image data.

Herein, the image data may, for example, include CT image data, MRT image data, or ultrasound-image data.

The image data may, for example, include a time series of images that depict the tissue region of the patient during the predefined movement of the patient, and the at least one material parameter of the tissue model may be determined based on the time series of images.

A further aspect of the present embodiments discloses a computer program with instructions. When the instructions are executed by a data processing apparatus containing at least one processor, the instructions cause the data processing apparatus to execute a computer-implemented method according to the present embodiments.

A further aspect of the present embodiments discloses a computer-readable storage medium (e.g., a non-transitory computer-readable storage medium) that stores a computer program according to the present embodiments.

The computer program and the computer-readable storage medium may be respective computer program products with the instructions.

A further aspect of the present embodiments discloses a data processing apparatus that includes at least one processor configured to execute a computer-implemented method according to the present embodiments.

A further aspect of the present embodiments discloses a therapeutic ultrasound apparatus (e.g., a histotripsy apparatus). The therapeutic ultrasound apparatus includes a data processing apparatus according to the present embodiments and an ultrasonic transducer (e.g., a histotripsy transducer) for emitting ultrasonic waves and a control unit. The control unit is set up to control the ultrasonic transducer according to the therapeutic plan in order to generate the plurality of lesions.

A computer-implemented method according to the present embodiments also discloses a therapeutic ultrasound method. Herein, a computer-implemented method according to the present embodiments is performed, and the plurality of lesions is generated by a therapeutic ultrasound apparatus (e.g., a therapeutic ultrasound apparatus according to the present embodiments) in a tissue region of a patient.

If it is mentioned in the context of the present disclosure that a component of the therapeutic ultrasound apparatus according to the present embodiments or the data processing apparatus according to the present embodiments (e.g., the at least one processor or the control unit) is set up, embodied, designed, or the like, to execute or realize a specific function, to achieve a specific effect, or to serve a specific purpose, this may be that, beyond the principal or theoretical usability or suitability for this function, effect, or this purpose, the component is specifically and actually capable of executing or realizing the function, achieving the effect, or serving the purpose by appropriate adaptation, programming, physical embodiment, and so on.

BRIEF DESCRIPTION OF THE DRAWING

FIG. 1 is a schematic representation of an embodiment of a therapeutic ultrasound apparatus.

DETAILED DESCRIPTION

FIG. 1 is a schematic representation of an exemplary embodiment of a therapeutic ultrasound that is, for example, configured as a histotripsy apparatus 1. The histotripsy apparatus 1 includes a data processing apparatus 2 that may execute a computer-implemented method according to the present embodiments for planning histotripsy therapy of a three-dimensional tissue region 7 of a patient 6. As a result of the computer-implemented method, the data processing apparatus 2 generates a therapeutic plan for the histotripsy therapy in order to change at least one material parameter relating to the deformability and/or elasticity of the corresponding material of the tissue region 7 in a predefined manner.

The histotripsy apparatus 1 also includes a control unit 4 and a histotripsy transducer 3 for emitting ultrasonic waves. The control unit 4 is set up to control the histotripsy transducer 3 according to the therapeutic plan obtained from the data processing apparatus 2 in order to generate a plurality of lesions in a treatment region 8 within the tissue region 7 by means of histotripsy.

Optionally, the histotripsy apparatus 1 may also include an ultrasound probe 5 for imaging, which may, for example, also be actuated by the control unit to enable the tissue region 7 or the treatment region 8 to be visually monitored during the histotripsy procedure.

In the context of the computer-implemented method for planning histotripsy therapy, initially, a three-dimensional tissue model of the tissue region 7 containing the at least one material parameter is provided in spatially resolved and/or directionally resolved form.

In some embodiments, the tissue model may include a deformable three-dimensional model of the tissue region that may be deformed in any spatial direction according to the tissue properties (e.g., according to the at least one material parameter, elasticity, deformability, stress, presence of calcification, etc.). The tissue model may also contain information relating to a load limit for forces or stresses acting on the tissue.

In some embodiments, the tissue model may be determined based on image data of the patient 6 acquired prior to the performance of the method from an elasticity measurement. The tissue model may also contain information on positions or regions of existing or previous inflammation, fractures, tears, or other healed or chronic pathological conditions.

In some embodiments, the tissue model may be determined based on a time series of image data of the patient 6 acquired prior to the performance of the method, where the time series depicts the tissue region 7 during a predefined movement of the patient 6. Herein, the at least one material parameter (e.g., the elasticity) or the load limit may be determined based on deformation of the tissue depicted by the time series and the information about the predefined movement of the patient 6.

Based on the tissue model, a part of the tissue region 7 is then determined as a treatment region 8 within which the lesions are to be generated. The treatment region 8 may be determined manually, semi-automatically, or automatically. The treatment region 8 may, for example, have different values of the at least one material parameter compared to a reference tissue (e.g., a tissue or vessel surrounding the treatment region 8). Alternatively or additionally, the treatment region 8 may be characterized by the presence or occurrence therein of mechanical forces or stresses that are above the load limit. The treatment region 8 may also contain a plurality of partial treatment regions that may be spatially separated from one another or may touch and/or overlap.

The therapeutic plan is then generated based on the tissue model and the treatment region 8 so that the at least one material parameter may be changed by the planned lesions in a predefined way.

Herein, the therapeutic plan contains, for example, at least one characterization parameter that characterizes a plurality of lesions that may be generated by the histotripsy apparatus 1 in the treatment region 8 with respect to spatial arrangement of the plurality of lesions and/or respective pose of the plurality of lesions and/or respective shape of the plurality of lesions. Alternatively or additionally, the therapeutic plan contains at least one configuration parameter for the histotripsy apparatus 1 for generating the plurality of lesions.

The therapeutic plan may, for example, specify an anisotropic spatial arrangement or an anisotropic spatial pattern consisting of the lesions in order in this way to change the elasticity and/or deformability of the tissue and/or the forces and/or stresses in the tissue region 7 to one or more target values or target specifications.

In various embodiments, the tissue model may be created based on information about critical regions, such as, for example, fibrotic structures, pre-existing lesions, vessels, calcification, and so on, within the tissue region 7. This information may be incorporated into the tissue model and thereby taken into account when defining the therapeutic plan. For example, the critical regions may be omitted when arranging the lesions. This may, for example, be formulated as a boundary condition during optimization (e.g., by the corresponding definition of a cost function).

For example, the at least one material parameter (e.g., the elasticity and/or deformability) may be taken into account anisotropically as a tensor. The objective may be increased or reduced elasticity and/or deformability along a specific direction, while the opposite may be desirable along another direction.

In one embodiment, the anisotropic spatial arrangement of the lesions may be determined such that, for example, all target values, target distributions, or other target specifications may be met. The lesions may be used in conjunction with pre-existing components of the tissue region 7 (e.g., fibrotic structures, scars, vessels, calcification, etc.) or in conjunction with pre-existing implants, such as, for example, stents, in order to achieve the target specifications.

Similarly to a foam mattress, the therapeutic plan may specify different zones with spatially arranged lesions of a different number, density, type, or shape. This enables the target specifications to be achieved.

The shape, density, and spatial arrangement of the lesions may reduce forces or stresses in order to accelerate healing processes or prevent the occurrence of disease or damage in the tissue region 7. The effect of histotripsy therapy may be temporary, for example, to accelerate the healing process, or permanent, for example, to prevent future damage.

The present embodiments enable planning of non-invasive histotripsy therapy for changing tissue properties (e.g., deformability and/or elasticity) in accordance with defined target specifications. This enables mobility and/or transport of fluids, such as blood, nutrients, or lymphatic fluid to be improved and/or pain to the patient 6 to be reduced.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for planning therapeutic ultrasound treatment of a three-dimensional tissue region, the computer-implemented method comprising:
   - providing a three-dimensional tissue model of the three-dimensional tissue region containing at least one material parameter relating to deformability, elasticity, or deformability and elasticity of a corresponding material of the three-dimensional tissue region in spatially resolved, directionally resolved, or spatially and directionally resolved form;
   - determining, based on the three-dimensional tissue model, part of the tissue region as a treatment region; and
   - depending on the three-dimensional tissue model and the treatment region, generating a therapeutic plan for the therapeutic ultrasound treatment, such that the at least one material parameter is changed in a predefined manner, wherein the therapeutic plan includes:

at least one characterization parameter that characterizes a plurality of lesions that are generatable by a therapeutic ultrasound apparatus in the treatment region with respect to spatial arrangement, respective pose, respective shape, or any combination thereof;

at least one configuration parameter for the therapeutic ultrasound apparatus for generating the plurality of lesions; or a combination thereof, wherein the therapeutic plan is created, such that the at least one characterization parameter characterizes an anisotropic distribution of the plurality of lesions to change the deformability, elasticity, or deformability and elasticity of the corresponding material of the three-dimensional tissue region.

2. The computer-implemented method of claim 1, further comprising:

determining, based on the three-dimensional tissue model, a load variable relating to a mechanical force acting on one or more parts of the tissue region, relating to a mechanical stress present in the tissue region, or relating to a combination thereof in a spatially resolved manner, in a directionally resolved manner, or in a spatially resolved and directionally resolved manner; and determining the treatment region depending on the load variable determined in the spatially resolved manner, in the directionally resolved manner, or in the spatially resolved and the directionally resolved manner.

3. The computer-implemented method of claim 2, wherein the load variable is determined in the spatially resolved manner, in the directionally resolved manner, or in the spatially resolved manner and in the directionally resolved manner based on the three-dimensional tissue model and a predefined movement of the tissue region.

4. The computer-implemented method of claim 2, further comprising comparing the load variable determined in the spatially resolved manner, in the directionally resolved manner, or in the spatially resolved manner and the directionally resolved manner with a prespecified load limit, wherein the treatment region is determined as part of the tissue region within which the load variable is determined in the spatially resolved manner, in the directionally resolved manner, or in the spatially resolved manner and in the directionally resolved manner is greater than the prespecified load limit.

5. The computer-implemented method of claim 2, wherein generating the therapeutic plan comprises:

minimizing the load variable, minimizing the load variable comprising varying the at least one characterization parameter, the at least one configuration parameter, or a combination thereof, or reducing the load variable, reducing the load variable comprising varying the at least one characterization parameter, the at least one configuration parameter, or a combination thereof to a value that is smaller than a prespecified maximum load limit.

6. The computer-implemented method of claim 2, further comprising:

applying a function trained by machine learning to input data that is dependent on the three-dimensional tissue model and the treatment region, such that output data that determines the at least one characterization parameter, the at least one configuration parameter, or a combination thereof is generated; and generating the therapeutic plan based on the output data.

7. The computer-implemented method of claim 6, further comprising:

modifying the three-dimensional tissue model according to the therapeutic plan;

determining the load variable again in the spatially resolved manner, in the directionally resolved manner, or in the spatially resolved manner and in the directionally resolved manner based on the modified three-dimensional tissue model; and generating a further therapeutic plan for the therapeutic ultrasound treatment depending on the load variable determined again in the spatially resolved manner, in the directionally resolved manner, or in the spatially resolved manner and in the directionally resolved manner.

8. The computer-implemented method of claim 7, further comprising comparing the load variable determined again in the spatially resolved manner, in the directionally resolved manner, or in the spatially resolved manner and in the directionally resolved manner with a prespecified load limit, wherein:

the further therapeutic plan is generated depending on a result of the comparison of the load variable determined again with the prespecified load limit and depending on the treatment region; or a further part of the tissue region is determined as a further treatment region depending on a result of the comparison, and the further therapeutic plan is generated depending on the further treatment region.

9. The computer-implemented method of claim 1, wherein the at least one material parameter includes a modulus of elasticity, a shear modulus, a bulk modulus, or any combination thereof.

10. The computer-implemented method of claim 1, wherein the therapeutic plan is generated such that the at least one characterization parameter is generated in the form of a binary map for the treatment region, and wherein the binary map stores a first value for positions at which one lesion of the plurality of lesions is provided and stores a second value that is different than the first value for positions at which no lesions of the plurality of lesions is provided.

11. The computer-implemented method of claim 1, further comprising providing image data that depicts the tissue region of a patient to be examined, wherein the tissue model is generated based on the image data.

12. The computer-implemented method of claim 1, wherein the therapeutic plan is created, such that the at least one characterization parameter characterizes the anisotropic distribution of the plurality of lesions to change the deformability, elasticity, or deformability and elasticity of the corresponding material of the three-dimensional tissue region to one or more target values or target specifications.

13. A non-transitory computer-readable storage medium that stores instructions executable by one or more processors to plan therapeutic ultrasound treatment of a three-dimensional tissue region, the instructions comprising:

providing a three-dimensional tissue model of the three-dimensional tissue region containing at least one material parameter relating to deformability, elasticity, or deformability and elasticity of a corresponding material of the three-dimensional tissue region in spatially resolved, directionally resolved, or spatially and directionally resolved form;

determining, based on the three-dimensional tissue model, part of the tissue region as a treatment region; and depending on the three-dimensional tissue model and the treatment region, generating a therapeutic plan for the therapeutic ultrasound treatment, such that the at least one material parameter is changed in a predefined manner, wherein the therapeutic plan includes:

at least one characterization parameter that characterizes a plurality of lesions that are generatable by a therapeutic ultrasound apparatus in the treatment region with respect to spatial arrangement, respective pose, respective shape, or any combination thereof;

at least one configuration parameter for the therapeutic ultrasound apparatus for generating the plurality of lesions; or a combination thereof, and wherein the therapeutic plan is created, such that the at least one characterization parameter characterizes an anisotropic distribution of the plurality of lesions to change the deformability, elasticity, or deformability and elasticity of the corresponding material of the three-dimensional tissue region.

14. The non-transitory computer-readable storage medium of claim 13, wherein the instructions further comprise:

determining, based on the three-dimensional tissue model, a load variable relating to a mechanical force acting on one or more parts of the tissue region, relating to a mechanical stress present in the tissue region, or relating to a combination thereof in a spatially resolved manner, in a directionally resolved manner, or in a spatially resolved and directionally resolved manner; and determining the treatment region depending on the load variable determined in the spatially resolved manner, in the directionally resolved manner, or in the spatially resolved and the directionally resolved manner.

15. The non-transitory computer-readable storage medium of claim 14, wherein the load variable is determined in the spatially resolved manner, in the directionally resolved manner, or in the spatially resolved manner and in the directionally resolved manner based on the three-dimensional tissue model and a predefined movement of the tissue region.

16. The non-transitory computer-readable storage medium of claim 14, wherein the instructions further comprise comparing the load variable determined in the spatially resolved manner, in the directionally resolved manner, or in the spatially resolved manner and the directionally resolved manner with a prespecified load limit, and wherein the treatment region is determined as part of the tissue region within which the load variable is determined in the spatially resolved manner, in the directionally resolved manner, or in the spatially resolved manner and in the directionally resolved manner is greater than the prespecified load limit.

17. A data processing apparatus comprising:

at least one processor configured to plan therapeutic ultrasound treatment of a three-dimensional tissue region, the plan of the therapeutic ultrasound treatment comprising:

provision of a three-dimensional tissue model of the three-dimensional tissue region containing at least one material parameter relating to deformability, elasticity, or deformability and elasticity of a corresponding material of the three-dimensional tissue region in spatially resolved, directionally resolved, or spatially and directionally resolved form;

determination, based on the three-dimensional tissue model, of part of the tissue region as a treatment region; and depending on the three-dimensional tissue model and the treatment region, generation of a therapeutic plan for the therapeutic ultrasound treatment, such that the at least one material parameter is changed in a predefined manner, wherein the therapeutic plan includes:

at least one characterization parameter that characterizes a plurality of lesions that are generatable by a therapeutic ultrasound apparatus in the treatment region with respect to spatial arrangement, respective pose, respective shape, or any combination thereof, at least one configuration parameter for the therapeutic ultrasound apparatus for generating the plurality of lesions; or a combination thereof, and wherein the therapeutic plan is created, such that the at least one characterization parameter characterizes an anisotropic distribution of the plurality of lesions to change the deformability, elasticity, or deformability and elasticity of the corresponding material of the three-dimensional tissue region.

* * * * *